(12) United States Patent
Haynie et al.

(10) Patent No.: US 11,820,841 B2
(45) Date of Patent: Nov. 21, 2023

(54) REDUCING ACCUMULATION OF C6+ HYDROCARBON COMPONENTS IN POLYOLEFIN GAS-PHASE REACTORS

(71) Applicant: ExxonMobil Chemical Patents Inc., Baytown, TX (US)

(72) Inventors: Steven P. Haynie, Dayton, TX (US); Giyarpuram N. Prasad, Houston, TX (US); Diwaker Singh, Choa Chu Kang-Central (SG); Gautam Swamynathan, Houston, TX (US); Stacy N. Apugo, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 772 days.

(21) Appl. No.: 16/864,519

(22) Filed: May 1, 2020

(65) Prior Publication Data
US 2020/0255564 A1    Aug. 13, 2020

Related U.S. Application Data

(60) Provisional application No. 62/966,673, filed on Jan. 28, 2020.

(51) Int. Cl.
*C08F 210/16* (2006.01)
*C08F 210/06* (2006.01)
(Continued)

(52) U.S. Cl.
CPC .............. *C08F 210/16* (2013.01); *B01D 3/14* (2013.01); *B01D 5/006* (2013.01); *B01D 5/009* (2013.01);
(Continued)

(58) Field of Classification Search
CPC ...... C08F 210/16; B01J 19/2465; C07C 7/04; B01D 5/006
(Continued)

(56) References Cited

U.S. PATENT DOCUMENTS

| 4,003,712 A | 1/1977 | Miller |
| 4,302,566 A | 11/1981 | Karol et al. |

(Continued)

*Primary Examiner* — Fred M Teskin
(74) *Attorney, Agent, or Firm* — ExxonMobil Technology and Engineering Company-Chemicals

(57) ABSTRACT

A polymerization process may include: polymerizing a monomer having 4 or less carbons and a comonomer having 6 or more carbons in the presence of an inert isomer/saturate of the comonomer to yield a product stream comprising a polymer, unreacted monomer, unreacted comonomer, and the inert isomer/saturate of the comonomer; separating the product stream into (a) a polymer stream and (b) an unreacted components stream; and separating the unreacted components stream in a distillation column into (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream.

19 Claims, 4 Drawing Sheets

(51) Int. Cl.
  *B01J 19/06*   (2006.01)
  *B01D 5/00*   (2006.01)
  *B01D 3/14*   (2006.01)
  *B01J 19/24*   (2006.01)

(52) U.S. Cl.
  CPC ........... *B01J 19/06* (2013.01); *B01J 19/2465* (2013.01); *C08F 210/06* (2013.01)

(58) Field of Classification Search
  USPC ........................................................ 528/501
  See application file for complete search history.

(56) References Cited

U.S. PATENT DOCUMENTS

| | | | |
|---|---|---|---|
| 4,588,790 A | 5/1986 | Jenkins, III et al. | |
| 5,066,736 A | 11/1991 | Dumain et al. | |
| 5,352,749 A | 10/1994 | DeChellis et al. | |
| 5,462,999 A | 10/1995 | Griffin et al. | |
| 5,834,571 A | 11/1998 | Bernier et al. | |
| 7,582,723 B2 | 9/2009 | Penzo et al. | |
| 7,741,430 B2 * | 6/2010 | Walworth | C08F 10/02 |
| | | | 526/909 |
| 7,837,950 B2 | 11/2010 | Company | |
| 8,642,827 B2 | 2/2014 | Van Der Schrick | |
| 8,883,918 B2 | 11/2014 | Mignon et al. | |
| 11,058,987 B2 | 7/2021 | Ji et al. | |
| 2004/0236040 A1 | 11/2004 | Mihan et al. | |
| 2008/0177012 A1 * | 7/2008 | Penzo | B01J 8/006 |
| | | | 422/131 |
| 2010/0004407 A1 | 1/2010 | Goossens et al. | |

* cited by examiner

REDUCING ACCUMULATION OF C6+ HYDROCARBON COMPONENTS IN POLYOLEFIN GAS-PHASE REACTORS

CROSS-REFERENCE TO RELATED APPLICATION

This application claims the benefit of U.S. Provisional Application 62/966,673 filed Jan. 28, 2020, entitled "Reducing Accumulation of C6+ Hydrocarbon Components In Polyolefin Gas-Phase Reactors", the entirety of which is incorporated by reference herein.

FIELD OF INVENTION

The present disclosure relates to polyolefin synthesis.

BACKGROUND

Polyolefin syntheses often include a monomer and a comonomer where the comonomer has a higher carbon-number than the monomer. For example, a polyethylene may be synthesized using ethylene monomer and 1-hexene comonomer. The comonomer is typically high purity like 99% and includes impurities that are primarily inert isomers (in the prescribed reaction) and saturates of the comonomer (e.g., 2-cis-hexene and hexane, respectively).

In a polyolefin synthesis after polymerization in a gas-phase reactor, the product stream is separated into a polymer stream and an unreacted components stream, which comprises unreacted monomer, unreacted comonomer, and the impurities from the comonomer feed (e.g., inert isomers and/or saturates of the comonomer). Because the unreacted components stream comprises unreacted monomer and comonomer, the unreacted components stream can be recycled back to the reactor as a recycle stream so that the unreacted monomer and unreacted comonomer as well as fresh monomer and fresh comonomer from the feed stream can be used in the polymerization reaction. As one skilled in the art will recognized, describing a stream as a polymer stream, a unreacted components stream, or the like does not limit the composition of said stream to be 100% polymer or 100% unreacted components but only that the stream comprises some level of polymer or the unreacted components, respectively.

A polyolefin synthesis is an exothermic process. Therefore, the reactants are injected at a lower temperature than the reactor temperature. The greater the difference between the reactor temperature and the reactant injection temperature, the greater the efficiency and production rate of the polymerization reaction. The upper limit of the reactor temperature is limited at least in part by the softening temperature of the resultant polyolefin because the closer the reactor temperature is to the softening temperature, the more sticky the polyolefin becomes. A sticky polyolefin can build up on the reactor sidewalls and clog downstream flow paths, which requires a shutdown to clean the system. One contributing factor to the stickiness of a polyolefin is the concentration of liquid hydrocarbons (e.g., C4+ hydrocarbons, especially C6+ hydrocarbons) that can solubilize or otherwise disperse in the polyolefin. Higher concentrations of these hydrocarbons solubilized in the polyolefin cause a lowering of the softening temperature of the polyolefin.

As described above, the unreacted components including the unreacted comonomer and the inert isomers and saturates of the comonomer are included in the recycle stream. For example, for comonomers having 6 or more carbons (C6+ comonomer), the concentration of the C6+ components increases over time, which reduces the softening temperature of the polyolefin and narrows the operating window of the reactor. To alleviate the tendency towards softening point depression as the polymerization process progresses over time, current processes vent and/or flare the unreacted components stream periodically throughout the polymerization process to lower the buildup of these species. For example, FIG. 1 illustrates how venting is used to control the C6+ components in a polyethylene reactor. Illustrated is a prophetic plot (based on real data) of the C6+ inert hydrocarbons (e.g., hexane and 2-cis-hexene) concentration (volume %) in the reactor over time and the corresponding amount of unreacted components stream that is sent to vent rather than recycled back to the reactor. After a brief initial period, the unreacted components stream is vented to a greater degree and the C6+ inert hydrocarbon concentration trends slightly upward but is relatively stabilized. Then, the amount of unreacted components stream sent to vent is greatly reduced and the C6+ inert hydrocarbon concentration increases significantly and to a point where the unreacted components stream needs to be vented to an even greater degree than before to get the C6+ inert hydrocarbon concentration in the reactor back in line.

The vented/flared unreacted components stream includes volatile organic compounds of environmental concerns. Further, other components in the polymerization process (e.g., nitrogen used for purging) are lost in the non-selective venting/flaring process, which wastes resources and increases costs.

SUMMARY OF INVENTION

The present disclosure relates to polyolefin synthesis methods and systems where unreacted components stream is further separated to produce a stream enriched with the C6+ components and a stream enriched with lighter species.

The present disclosure includes a method comprising: polymerizing a monomer having 4 or less carbons (C4– monomer) and a comonomer having 6 or more carbons (C6+ comonomer) in the presence of an inert isomer of the comonomer and/or a saturate of the comonomer (known hereinafter as "inert isomer/saturate of the comonomer") to yield a product stream comprising a polymer, unreacted monomer, unreacted comonomer, and the inert isomer/saturate of the comonomer; separating the product stream into two or more streams comprising: (a) a polymer stream comprising the polymer and (b) an unreacted components stream comprising the unreacted monomer, unreacted comonomer, and the inert isomer/saturate of the comonomer; and separating the unreacted components stream in a distillation column into two or more streams comprising: (a) an overhead stream comprising the unreacted monomer and (b) a bottoms stream comprising the comonomer and the inert isomer/saturate of the comonomer, wherein a concentration of C5– hydrocarbons in the overhead stream is higher than a concentration of the C5– hydrocarbons in the unreacted components stream, and wherein a concentration of C6+ hydrocarbons in the bottoms stream is higher than a concentration of the C6+ hydrocarbons in the unreacted components stream.

The present disclosure also includes a system comprising: a polymerization reactor fluidly coupled to a polymer separation zone configured to receive a product stream from the polymerization reactor and separate the polymer product into two or more streams comprising: (a) a polymer stream comprising a polymer and (b) an unreacted components stream comprising (i) an unreacted monomer, (ii) an unreacted comonomer, and (iii) an inert isomer/saturate of the comonomer; an unreacted components separation zone fluidly coupled to the polymer separation zone and configured to receive the unreacted components stream from the polymer separation zone and separate the unreacted components stream into two or more streams comprising: (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream; and wherein the polymerization reactor fluidly coupled to unreacted components separation zone and configured to receive the overhead stream from the unreacted components separation zone.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

As used herein, "Cn" refers to hydrocarbons having n number of carbons. As used herein, "Cn−" refers to one or more hydrocarbons having n or fewer number of carbons (e.g., C5− can comprise C5 hydrocarbons, C4 hydrocarbons, and C3 hydrocarbons, alternatively C5− can comprise C4 hydrocarbons). As used herein, "Cn+" refers to one or more hydrocarbons having n or more number of carbons (e.g., C6+ can comprise C6 hydrocarbons, C7 hydrocarbons, and C8 hydrocarbons, alternatively C6+ can comprise C6 hydrocarbons, alternatively C6+ can comprise C8 hydrocarbons).

The present disclosure relates to polyolefin synthesis methods and systems where an unreacted components stream is further separated to produce a stream enriched with the C6+ components (e.g., comonomers, inert isomers of the comonomer, and/or saturates of the comonomer) and a stream for recycling to the polymerization reaction that is enriched with lighter species (e.g., C5− hydrocarbons, nitrogen, and/or argon). Advantageously, the methods and systems described herein (1) improve the polymerization efficiency and production rate by reducing the concentration of C6+ components in a gas-phase reactor so as to increase the softening temperature of the polyolefin product while (2) reducing emissions and reactant/diluent costs by having a recycle stream that is enriched with lighter species like C5− hydrocarbon reactants, C5− hydrocarbon diluents, and non-hydrocarbon diluents.

The systems and methods described herein may be implemented in various polyolefin syntheses that employ a C4− monomer (hereinafter "monomer") and a C6+ comonomer (hereinafter "comonomer"). Examples of monomer/comonomer combinations include, but are not limited to, ethylene/1-hexene, ethylene/1-octene, propylene/1-hexene, propylene/1-octene, ethylene and propylene/1-hexene, ethylene and propylene/1-octene, and the like. In the last two examples, a mixture of ethylene and propylene are considered the monomer portion herein, where either the ethylene or the propylene may be at a higher concentration than the other.

Figure 1:
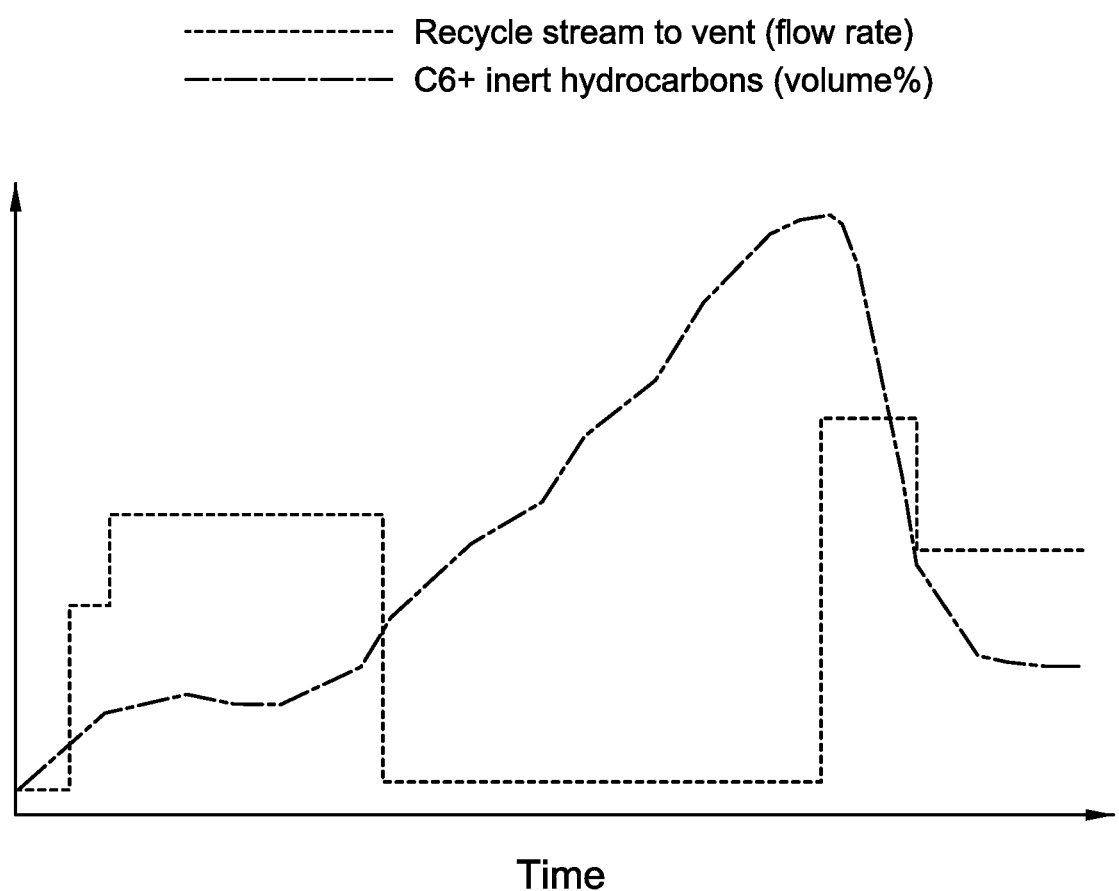
FIG. 1 illustrates a prophetic plot (based on real data) of the C6+ inert hydrocarbons (e.g., hexane and 2-cis-hexene) concentration (volume %) in a gas-phase reactor over time and the corresponding amount of unreacted components stream that is sent to vent rather than recycled back to the reactor.
Figure 2:
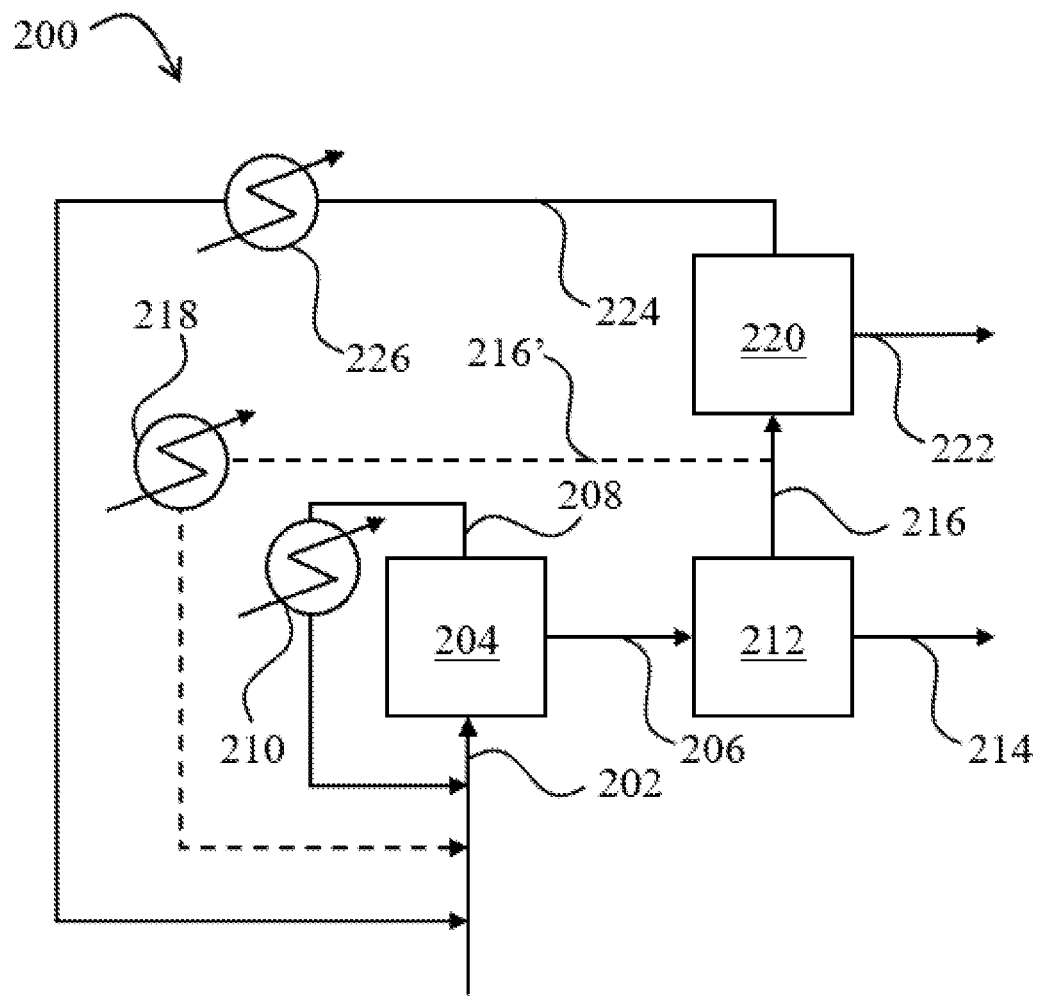
FIG. 2 illustrates a diagram of a nonlimiting example of a process of the present disclosure.

FIG. 2 illustrates a diagram of a nonlimiting example of a process 200 of the present disclosure. The process 200 includes injecting a feed stream 202 comprising (a) a monomer, (b) a comonomer, and (c) an inert isomer/saturate of the comonomer (wherein "inert isomer/saturate of the comonomer" refers to an inert isomer of the comonomer, a saturate of the comonomer, or a combination thereof) into a gas-phase reactor 204. The monomer and comonomer react in the presence of a catalyst in the reactor 204 to yield (a) a product stream 206 comprising a polymer, unreacted monomer, unreacted comonomer, and the inert isomer/saturate of the comonomer and (b) a recycle stream 208 comprising an unreacted monomer, unreacted comonomer, and the inert isomer/saturate of the comonomer. The recycle stream 208 is cooled, for example, by heat exchanger 210 and fed back into the reactor 204. If diluent components are used like inert C5− hydrocarbons (e.g., propane, a n-butane, i-butane, n-pentane, i-pentane, and any combination thereof), nitrogen, argon, and any combination thereof in the process, said diluent components would also be present in the feed stream 202, the product stream 206, and the recycle stream 208.

In the illustrated example, there is only one stream, the feed stream 202, introduced directly to the reactor, and the other streams recycled back (e.g., the recycle stream 208, a portion 216' of the unreacted components stream 216, and an overhead stream 224) are admixed with the feed stream 202 before introduction to the reactor 204. However, the various streams may be admixed in any combination and/or introduced as separate streams.

The product stream 206 is conveyed to a polymer separation zone 212 where the polymer is separated from the unreacted components to produce a polymer stream 214 and an unreacted components stream 216, respectively. Other streams (not illustrated) may also be produced from the polymer separation zone 212. The systems and methods suitable to be employed in the polymer separation zone 212 are known in the art and may include components like cyclones, filters, strippers, purge units (also referred to as purge bins), degassers, and the like. As will be apparent to those skilled in the art, the efficacy of separating the polymer from the unreacted components may vary based on the methods employed. Further, as will be apparent to one skilled in the art, polyolefin syntheses are conducted in the presence of a catalyst, which is not illustrated in FIG. 2. The processes and hardware of the reactor 204 and the polymer separation zone 212 may be any of those known in the art. Nonlimiting examples of polyolefin syntheses, reactors, and/or corresponding separation zones/processes are described in U.S. Pat. Nos. 4,003,712, 4,588,790, 4,302,566, 5,066,736, 5,352,749, 5,462,999, 5,834,571, and 7,837,950 and US Patent Application Publication Nos. 2004/0236040 and 2010/0004407, which are incorporated herein by reference.

As described above, the unreacted components stream 216 from the polymer separation zone 212 is typically recycled back to the reactor 204. The methods and systems described herein further include an unreacted components separation zone 220 where at least a portion of the unreacted components stream 216 is further separated into two or more streams that include, but are not limited to, an overhead stream 224 comprising the unreacted monomer and a bottoms stream 222 comprising the unreacted comonomer and the inert isomers/saturate of the comonomer. The unreacted components separation zone 220 includes a distillation column for separating the C6+ components in the unreacted components stream 216 from the C5− components in the unreacted components stream 216. Therefore, a concentration of the C6+ components (e.g., comonomer and inert isomers/saturate of the comonomer) in the overhead stream 224 is lower than a concentration of the C6+ components in the unreacted components stream 216, and the concentration of the C6+ components in the bottoms stream 222 is higher than the concentration of the C6+ components in the unreacted components stream 216. The overhead stream 224 is recycled back to reactor 204 for further polymerization reaction. Advantageously, the overhead stream 224 has less C6+ components that dissolve in the polyolefin product and reduce the softening temperature of said polyolefin product. Therefore, the reactor 204 can be operated at a sustained higher temperature without risking fouling, which results in a sustained higher temperature difference between the reactor temperature and the reactant injection temperature and a more efficient and higher throughput polyolefin production.

For example, in a polyethylene synthesis using ethylene and 1-hexene as described above, the distillation column would be configured to separate C5− components (overhead stream 224) and C6+ components (the bottoms stream 222). Again, separations are not perfect, so C6+ components may be in the overhead stream 224, and C5− components may be in the bottoms stream 222. However, the overhead stream 224 is enriched in C5− components as compared to the unreacted components stream 216, and the bottoms stream 222 is enriched in C6+ components as compared to the unreacted components stream 216. The overhead stream 224 is recycled back to reactor 204 for further polymerization reaction. Advantageously, the overhead stream 224 has less C6+ components that reduce the softening temperature of the polyethylene. Therefore, the reactor 204 can be operated at a sustained higher temperature, which results in a sustained higher temperature difference between the reactor temperature and the reactant injection temperature and a more efficient and higher throughput production.

The bottoms stream 222 can be vented, flared, or used in other processes in the plant or facility. For example, the bottoms stream 222 can be used as fuel feed in a boiler or similar equipment. Advantageously, the bottoms stream 222 has less volatile organic compounds than the unreacted components stream 216, which is typically the stream that is vented, flared, or used in other processes. Accordingly, the systems and methods of the present disclosure reduce the amount of volatile organic compounds and/or carbon dioxide emissions resultant from the combustion product from flare.

The overhead stream 224 and any other stream from the unreacted components separation zone 220 having a concentration of the C6+ components that is lower than the concentration of the C6+ components in the unreacted components stream 216 may be recycled back to the reactor 204. Enriching the C5− components and reducing the C6+ components in the streams recycled back to the reactor 204 is less wasteful of the reactants as well as diluent hydrocarbons and nitrogen used in the process and, therefore, presents cost savings as well as environmental advantages.

The overhead stream 224 and any other stream from the unreacted components separation zone 220 that is enriched with C5− components (e.g., unreacted monomer and hydrocarbon diluents) may have a cumulative wt % concentration of C5− components in said stream ($[C5-]_O$) that is 1.1 times or more (or 1.1 times to 100 times or more, or 1.1 times to 5 times, or 1.5 times to 10 times, or 5 times to 35 times, or 25 times to 75 times, or 50 times to 100 times) greater than a cumulative wt % concentration of C5− components in the unreacted components stream 216 ($[C5-]_{UC}$). Such a calculation is performed $[C5-]_O/[C5-]_{UC}$ where concentrations are wt % based on total weight of C components in the respective streams.

The bottoms stream 222 may have a cumulative wt % concentration of C6+ components (e.g., the unreacted comonomer, the inert isomer of the comonomer, and the saturate of the comonomer) in the bottoms stream 222 ($[C6+]_B$) that is 1.5 times or more (or 1.5 times to 100 times or more, or 1.5 times to 20 times, or 5 times to 35 times, or 25 times to 75 times, or 50 times to 100 times) greater than a cumulative wt % concentration of C6+ components in the unreacted components stream 216 ($[C6-]_{UC}$). Such a calculation is performed $[C6+]_B/[C6+]_{UC}$ where concentrations are wt % based on total weight of C components in the respective streams.

Depending on how low the concentration is of the C6+ components being recycled back from the unreacted components separation zone 220, a portion 216' of the unreacted components stream 216 may be recycled back to the reactor 204.

In the illustrated example of FIG. 2, the streams 208, 216', and 224 recycled back to the reactor 204 pass through respective heat exchangers 210, 218, and 226, which is used to maintain a suitable low temperature for the reactants being introduced to the feed stream 202. Again, streams 208, 216', and 224 recycled back to the reactor 204 may be introduced separately and/or admixed in any combination. Accordingly, the placement and number of heat exchangers may be different from the illustration of this nonlimiting example.

Further, as will be apparent to those skilled in the art, the systems and methods illustrated in this nonlimiting example may include additional components like compressors, membranes, valves, flow meters, heat exchangers, traps, and the like for proper and safe operation of said systems and methods.

Figure 3:
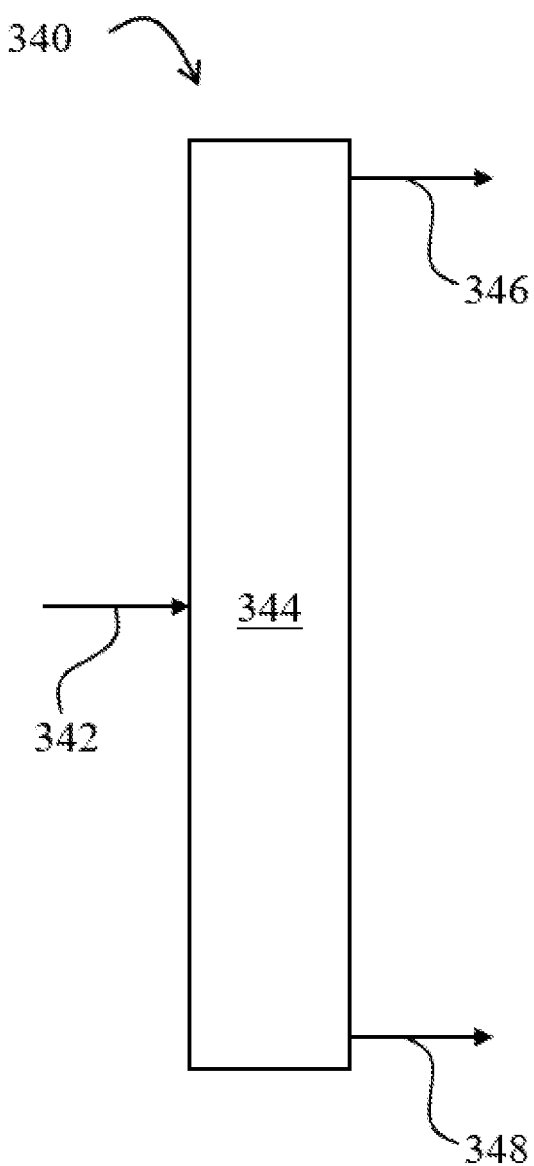
FIG. 3 illustrates a diagram of a nonlimiting example of an unreacted components separation zone of the present disclosure.

FIG. 3 illustrates a diagram of a nonlimiting example of an unreacted components separation zone 340 of the present disclosure. An unreacted components stream 342 (e.g., unreacted components stream 216 of FIG. 2) is introduced to a distillation column 344. Distillation proceeds at a temperature and pressure sufficient to produce an overhead stream 346 (e.g., overhead stream 224 of FIG. 2) enriched in C5− components and a bottoms stream 348 (e.g., bottoms stream 222 of FIG. 2) enriched in C6+ components.

The distillation column 344 may have any suitable configuration. In one nonlimiting example, the distillation column 344 may be a packed bed column where the particles in the packed bed provide increased surface area for more effective and more efficient separations. In such examples, the particles of the packed bed should be nonreactive with the components of the unreacted components stream 342 at the distillation conditions. In another nonlimiting example, the distillation column 344 may be a tray column.

Figure 4:
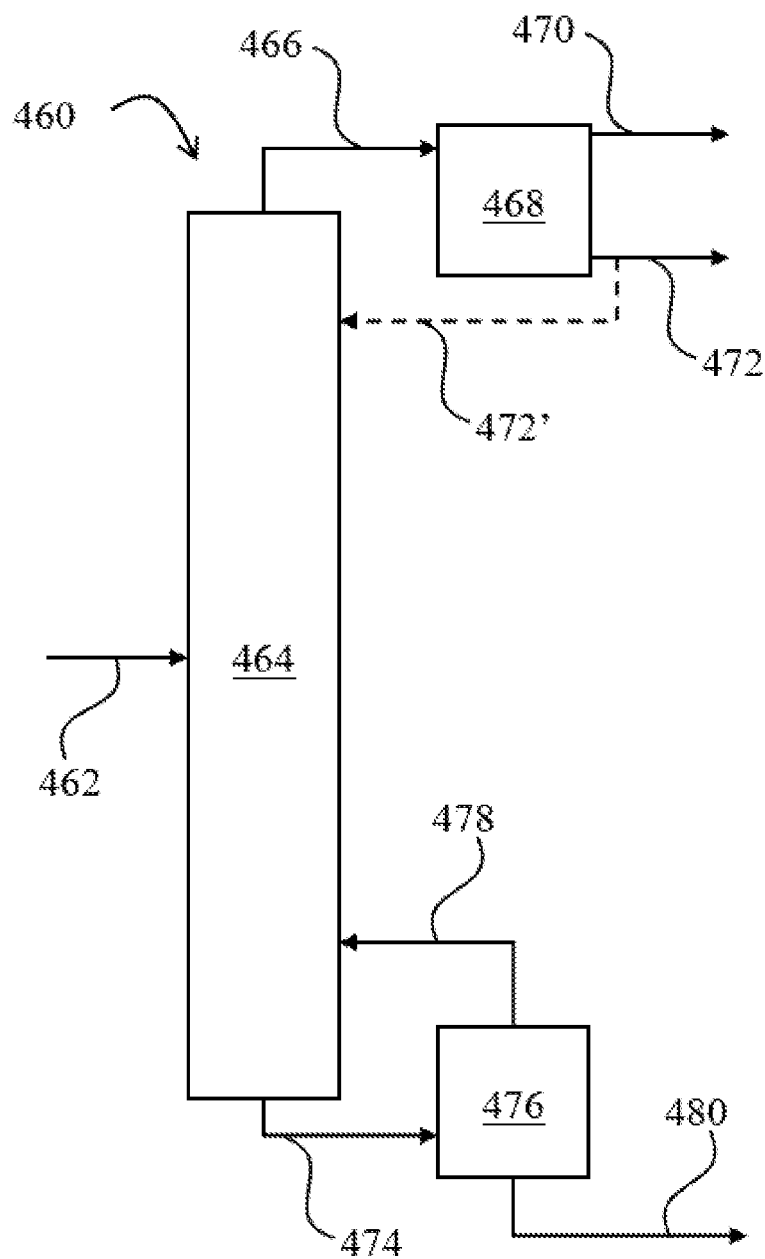
FIG. 4 illustrates a diagram of another nonlimiting example of an unreacted components separation zone of the present disclosure.

FIG. 4 illustrates a diagram of another nonlimiting example of an unreacted components separation zone 460 of the present disclosure. An unreacted components stream 462 (e.g., unreacted components stream 216 of FIG. 2) is introduced to a distillation column 464. Distillation proceeds at a temperature and pressure sufficient to produce an overhead stream 466 enriched in C5− components and a bottoms stream 474 enriched in C6+ components.

The overhead stream 466 may be further separated by cooling the overhead stream 466 and flashing the cooled overhead stream 466 into a condenser 468 (e.g., a partial condenser or a full condenser). In a partial condenser, the condenser 468 evaporates the most volatile components (e.g., C2-C4 components and diluents) while the less volatile components (e.g., C5 components and any minor amounts of C6+ components) in the overhead stream 466 remain liquid, thereby producing a vapor overhead stream 470 and a liquid overhead stream 472, respectively. One or both of the vapor overhead stream 470 and the liquid overhead stream 472 may be recycled back to the reactor (e.g., as overhead stream 224 of FIG. 2). Again, one or both of the vapor overhead stream 470 and the liquid overhead stream 472 may be recycled back to the reactor for direct injection or may be admixed with another recycle stream. Optionally, a portion 472' of the liquid overhead stream 472 may be recycled back to the distillation column 464.

The bottoms stream 474 may be further separated by heating the bottoms stream 474 in a reboiler 476. The reboiler 476 evaporates the most volatile components (e.g., reactive C5− components and diluents like inert C5− hydrocarbons, nitrogen, argon, and any combination) while the less volatile components (e.g., the C6+ components) in the bottoms stream 474 remain liquid, thereby producing a vapor bottoms stream 478 and a liquid bottoms stream 480 (e.g., bottoms stream 222 of FIG. 2), respectively. The vapor bottoms stream 478 may be recycled back into the distillation column 464. The liquid bottoms stream 480 can be vented, flared, used as fuel feed, or the like.

The distillation column 464 may have any suitable configuration. In one nonlimiting example, the distillation column 464 may be a packed bed column where the particles in the packed bed provide increased surface area for more effective and more efficient separations. In such examples, the particles of the packed bed should be nonreactive with the components of the unreacted components stream 462 at the distillation conditions. In another nonlimiting example, the distillation column 464 may be a tray column.

Further, as will be apparent to those skilled in the art, the systems and methods illustrated in the foregoing nonlimiting examples may include additional components like compressors, valves, flow meters, heat exchangers, traps, and the like for proper and safe operation of said systems and methods.

In other alternative configurations for the unreacted components separation zone 220, only the overhead stream 466 or only the bottoms stream 474 may be further separated. One skilled in the art will recognize other configurations for the unreacted components separation zone 220 consistent with the methods of the present disclosure.

Further, as will be apparent to those skilled in the art, several reactors may be running in parallel. Optionally, two or more reactors can feed polymer product to a polymer separation zone. Further, if two or more polymer separation zones are running in parallel, the unreacted components streams can be admixed or added to the same distillation column. Further, the recycle streams from one or more distillation columns can be used to feed one or more reactors. One skilled in the art will recognize the suitable configurations based on the capacity of the reactors, polymer separation zones, and distillation columns.

Example Embodiments

A first nonlimiting example embodiment of the present disclosure is a method comprising: polymerizing a C4− monomer and a C6+ comonomer in the presence of an inert isomer/saturate of the comonomer to yield a product stream comprising a polymer, unreacted monomer, unreacted comonomer, and the inert isomer/saturate of the comonomer; wherein the inert isomer/saturate of the comonomer is an inert isomer of the comonomer, a saturate of the comonomer, or a combination thereof; separating the product stream into two or more streams comprising: (a) a polymer stream comprising the polymer and (b) an unreacted components stream comprising the unreacted monomer, unreacted comonomer, and the inert isomer/saturate of the comonomer; and separating the unreacted components stream in a distillation column into two or more streams comprising: (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream. The first nonlimiting example embodiment may further include one or more of the following: Element 1: wherein the concentration of the C5− hydrocarbons in the overhead stream is 1.1 or more times (or 1.1 times to 100 times or more, or 1.1 times to 5 times, or 1.5 times to 10 times, or 5 times to 35 times, or 25 times to 75 times, or 50 times to 100 times) higher than a concentration of the C5− hydrocarbons in the unreacted components stream; Element 2: wherein the concentration of C6+ hydrocarbons in the bottoms stream is 1.5 or more times (or 1.5 times to 100 times or more, or 1.5 times to 20 times, or 5 times to 35 times, or 25 times to 75 times, or 50 times to 100 times) higher than a concentration of the C6+ hydrocarbons in the unreacted components stream; Element 3: wherein separating the unreacted components stream comprises: distilling the unreacted components stream through a packed bed column and/or a tray column; Element 4: the method further comprising: recycling the overhead stream into a polymerization reaction; Element 5: Element 4 and the method further comprising: cooling the overhead stream before recycling the overhead stream into the polymerization reaction; Element 6: wherein the bottoms stream is a first bottoms stream and the overhead stream is a first overhead stream, and wherein the method further comprises: cooling the first overhead stream into two or more streams comprising: (a) a second overhead stream and (b) a second bottoms stream; recycling the second bottoms stream into the distillation column; and recycling the second overhead stream into the polymerization reaction; Element 7: Element 6 and wherein the two or more streams from the first overhead stream further comprises (c) a liquids stream, and wherein the method further comprises: recycling the liquids stream into the polymerization reaction; Element 8: Element 6 and wherein the method further comprises: heating the first bottoms stream into two or more streams comprising: (a) a third overhead stream and (b) a third bottoms stream; and recycling the second overhead stream into the distillation column; Element 9: wherein the bottoms stream is a first bottoms stream and the overhead stream is a first overhead stream, and wherein the method further comprises: heating the first bottoms stream into two or more streams comprising: (a) a second overhead stream and (b) a second bottoms stream; and recycling the second overhead stream into the distillation column; Element 10: the method further comprising: performing polymerizing the monomer and the comonomer and separating the product stream occur in parallel in two or more reaction zones and corresponding separation zones; and wherein two or more the unreacted components streams corresponding to the two or more reaction zones and corresponding separation zones are combined before separating the unreacted components stream; Element 11: wherein the monomer comprises ethylene, the comonomer comprises 1-hexene, and the inert isomer/saturate of the comonomer comprises hexane; Element 12: wherein the monomer comprises ethylene, the comonomer comprises 1-octene, and the inert isomer/saturate of the comonomer comprises octane; Element 13: wherein the monomer comprises propylene, the comonomer comprises 1-hexene, and the inert isomer/saturate of the comonomer comprises hexane; Element 14: wherein the monomer comprises propylene, the comonomer comprises 1-octene, and the inert isomer/saturate of the comonomer comprises octane; Element 15: wherein the monomer comprises ethylene and propylene, the comonomer comprises 1-hexene, and the inert isomer/saturate of the comonomer comprises hexane; Element 16: wherein the monomer comprises ethylene and propylene, the comonomer comprises 1-octene, and the inert isomer/saturate of the comonomer comprises octane; Element 17: wherein polymerizing occurs further in the presence of an inert C5− hydrocarbon; and Element 18: Element 17 and wherein the C5− inert hydrocarbon comprises propane, n-butane, i-butane, n-pentane, i-pentane, and any combination thereof. Examples of combinations include, but are not limited to, two or more of Elements 1-3 in combination; one or more of Elements 1-3 in combination with Element 4 and optionally Element 5; one or more of Elements 1-3 in combination with Element 6 and optionally Element 7 and/or Element 8; one or more of Elements 1-5 in combination with Element 9; one or more of Elements 10-18 in combination with one or more of Elements 1-9; Element 17 and optionally Element 18 in combination with one or more of Elements 10-16; one or more of Elements 10-16 in combination with Element 4 and optionally Element 5; and one or more of Elements 10-16 in combination with Element 6 and optionally Element 7 and/or Element 8.

A second nonlimiting example embodiment is a system comprising: a polymerization reactor fluidly coupled to a polymer separation zone configured to receive a product stream from the polymerization reactor and separate the polymer product into two or more streams comprising: (a) a polymer stream comprising a polymer and (b) an unreacted components stream comprising (i) an unreacted monomer, (ii) an unreacted comonomer, and (iii) an inert isomer of the comonomer and/or a saturate of the comonomer (inert isomer/saturate of the comonomer); an unreacted components separation zone fluidly coupled to the polymer separation zone and configured to receive the unreacted components stream from the polymer separation zone and separate the unreacted components stream into two or more streams comprising: (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream; and wherein the polymerization reactor fluidly coupled to the unreacted components separation zone and configured to receive the overhead stream from the unreacted components separation zone. The second nonlimiting example embodiment may further include one or more of the following: Element 11; Element 12; Element 13; Element 14; Element 15; Element 16; Element 17; Element 18; Element 19: wherein the distillation column is a packed bed column and/or a tray column; Element 20: wherein the separation zone comprises a distillation column fluidly coupled to the polymer separation zone and configured to receive the unreacted components stream from the polymer separation zone; Element 21: Element 20 and wherein the overhead stream is a first overhead stream, and wherein the separation zone comprises a condenser fluidly coupled to the distillation column and configured to receive a second overhead stream from the distillation column and produce the first overhead stream; Element 22: Element 20 and wherein the bottoms stream is a first bottoms stream, and the separation zone comprises a reboiler configured to receive a second bottoms stream from the distillation column and produce (a) a vapor bottoms stream and (b) a liquid bottoms stream, wherein the distillation column is also configured to receive the vapor bottoms stream from the reboiler; and Element 23: Element 20 and wherein the overhead stream is a first overhead stream, and wherein the separation zone comprises a condenser fluidly coupled to the distillation column and configured to receive a second overhead stream from the distillation column and produce the first overhead stream, wherein the bottoms stream is a first bottoms stream, and the separation zone comprises a reboiler configured to receive a second bottoms stream from the distillation column and produce (a) a vapor bottoms stream and (b) a liquid bottoms stream, and wherein the distillation column is also configured to receive the vapor bottoms stream from the reboiler. Examples of combinations include, but are not limited to; two of Elements 11-18 in combination; one or more of Elements 11-18 in combination with Element 19 and/or Element 20; one or more of Elements 11-18 in combination with Element 20 and optionally one of Elements 21-23; and Element 20 in combination with one of Elements 21-23 and optionally in further combination with one or more of Elements 11-19.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Example 1

A distillation separation simulation was performed using a ProII program, 10.2 version, available from SimSci. In the simulation, a feed having a composition, which is reasonable for an unreacted components stream from a typical separation of the product stream of a polymerization reaction, is fed into a packed bed distillation column near the middle of the column. The distillation column produces a bottoms stream and an overhead stream. The overhead stream is separated into an overhead gas stream and an overhead liquid stream. The compositions (based on a mass rate (kg/hr)) and conditions for each of the four streams (feed stream, bottoms stream, overhead gas stream, and overhead liquid stream) are provided in Table 1.

This example illustrates that the distillation column can be used to enrich the C6 components (e.g., including comonomer and inert isomers/saturate of the comonomer) in a bottoms stream, which, consequently, enriches the C5− components in the two overhead stream. The one or both of the two overhead streams may be recycled back via any suitable routing to a polymerization reaction. Advantageously, the two overhead streams are lower than the feed stream (which would be the unreacted components stream described above) in C6 components, which can make the polyethylene sticky in the reactor as described herein. Therefore, the methods described herein advantageously produce recycle streams with reduced C6+ components that reduce the softening temperature of the polyolefin in the reactor.

Example 2

A distillation separation simulation was performed using a ProII program, 10.2 version, available from SimSci. In the simulation, a feed having a composition, which is reasonable for an unreacted components stream from a typical separation of the product stream of a polymerization reaction, is fed into a packed bed distillation column near the middle of the column. The distillation column produces a bottoms stream and an overhead stream. The overhead stream is separated into an overhead gas stream and an overhead liquid stream. The compositions (based on a mass rate (kg/hr)) and conditions for each of the four streams (feed stream, bottoms stream, overhead gas stream, and overhead liquid stream) are provided in Table 2.

TABLE 1

|  | Feed Stream (Unreacted Components Stream) | Bottoms Stream | Overhead Stream Gas | Overhead Stream Liquid |
|---|---|---|---|---|
| Conditions | | | | |
| Temperature (° C.) | −20 | 94 | 52 | 52 |
| Pressure (psig) | 144 | 40 | 30 | 30 |
| Composition based on Mass Rate (kg/hr) | | | | |
| hydrogen | 0 (0) | 0 (0) | 0 (0) | 0 (0) |
| nitrogen | 4.6 (0.46) | 0 (0) | 4.6 (1.27) | 0 (0) |
| methane | 0.1 (0.01) | 0 (0) | 0.1 (0.03) | 0 (0) |
| ethene | 53.3 (0.53) | 0 (0) | 51.6 (14.30) | 1.7 (0.49) |
| ethane | 1.8 (0.18) | 0 (0) | 1.7 (0.47) | 0.1 (0.03) |
| isopentane | 704.7 (7.04) | 100.6 (34.25) | 293.1 (81.21) | 311.0 (90.01) |
| 1-hexene | 111.1 (11.11) | 88.1 (30) | 5.6 (1.55) | 17.4 (5.04) |
| 2-cis-hexene | 62.1 (6.21) | 52.4 (17.84) | 2.1 (0.58) | 7.6 (2.20) |
| Hexane | 62.4 (6.24) | 52.6 (17.91) | 2.1 (0.58) | 7.7 (2.23) |
| Enrichment | | | | |
| $[C5-]_O/[C5-]_{UC}$ | n/a | n/a | 1.3 | 1.2 |
| $[C6+]_B/[C6+]_{UC}$ | n/a | 2.8 | n/a | n/a |

TABLE 2

| | Feed Stream (Unreacted Components Stream) | Bottoms Stream | Overhead Stream Gas | Overhead Stream Liquid |
|---|---|---|---|---|
| Conditions | | | | |
| Temperature (° C.) | −20 | 94 | 52 | 52 |
| Pressure (psig) | 144 | 40 | 30 | 30 |
| Composition based on Mass Rate (kg/hr) (Composition based on Wt %) | | | | |
| hydrogen | 0 (0) | 0 (0) | 0 (0) | 0 (0) |
| nitrogen | 4.7 (0.47) | 0 (0) | 4.5 (4.2) | 0.2 (0.03) |
| methane | 0.1 (0.01) | 0 (0) | 0.1 (0.09) | 0 (0) |
| ethene | 55.7 (5.57) | 0 (0) | 40.0 (37.28) | 14.7 (1.96) |
| ethane | 1.9 (0.19) | 0 (0) | 1.2 (1.12) | 0.7 (0.09) |
| isopentane | 771.2 (77.12) | 13.1 (9.24) | 60.5 (56.38) | 697.5 (93) |
| 1-hexene | 107.1 (10.71) | 78.0 (55.05) | 0.8 (0.75) | 28.3 (3.77) |
| 2-cis-hexene | 29.7 (2.97) | 25.3 (17.85) | 0.1 (0.09) | 4.3 (0.57) |
| hexane | 29.7 (2.97) | 25.3 (17.85) | 0.1 (0.09) | 4.3 (0.57) |
| Enrichment | | | | |
| $[C5-]_O/[C5-]_{UC}$ | n/a | n/a | 1.2 | 1.1 |
| $[C6+]_B/[C6+]_{UC}$ | n/a | 5.5 | n/a | n/a |

This example illustrates that the distillation column can be used to enrich the C6 components in a bottoms stream, which, consequently, enriches the C5− components in the two overhead stream. The one or both of the two overhead streams may be recycled back via any suitable routing to a polymerization reaction. Advantageously, the two overhead streams are lower than the feed stream (which would be the unreacted components stream described above) in C6 components, which can make the polyethylene sticky in the reactor as described herein. Therefore, the methods described herein advantageously produce recycle streams with reduced C6+ components that reduce the softening temperature of the polyolefin in the reactor.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
   polymerizing a C4− monomer and a C6+ comonomer in the presence of an inert isomer/saturate of the comonomer to yield a product stream comprising a polymer, unreacted monomer, unreacted comonomer, and the inert isomer/saturate of the comonomer;
   wherein the inert isomer/saturate of the comonomer is an inert isomer of the comonomer, a saturate of the comonomer, or a combination thereof;
   separating the product stream into streams comprising: (a) a polymer stream comprising the polymer and (b) an unreacted components stream comprising the unreacted monomer, unreacted comonomer, and the inert isomer/saturate of the comonomer; and
   separating the unreacted components stream in a distillation column into streams comprising: (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream.

2. The method of claim 1, wherein the concentration of the C5− hydrocarbons in the overhead stream is 1.1 or more times higher than a concentration of the C5− hydrocarbons in the unreacted components stream.

3. The method of claim 1, wherein the concentration of C6+ hydrocarbons in the bottoms stream is 1.5 or more times higher than a concentration of the C6+ hydrocarbons in the unreacted components stream.

4. The method of claim 1, wherein separating the unreacted components stream comprises:
   distilling the unreacted components stream through a packed bed column and/or a tray column.

5. The method of claim 1 further comprising:
recycling the overhead stream into a polymerization reaction.

6. The method of claim 5 further comprising:
cooling the overhead stream before recycling the overhead stream into the polymerization reaction.

7. The method of claim 1, wherein the bottoms stream is a first bottoms stream and the overhead stream is a first overhead stream, and wherein the method further comprises:
cooling the first overhead stream into two or more streams comprising: (a) a second overhead stream and (b) a second bottoms stream;
recycling the second bottoms stream into the distillation column; and
recycling the second overhead stream into the polymerization reaction.

8. The method of claim 7, wherein the two or more streams from the first overhead stream further comprises (c) a liquids stream, and wherein the method further comprises:
recycling the liquids stream into the polymerization reaction.

9. The method of claim 7 further comprises:
heating the first bottoms stream into two or more streams comprising: (a) a third overhead stream and (b) a third bottoms stream; and
recycling the second overhead stream into the distillation column.

10. The method of claim 1, wherein the bottoms stream is a first bottoms stream and the overhead stream is a first overhead stream, and wherein the method further comprises:
heating the first bottoms stream into two or more streams comprising: (a) a second overhead stream and (b) a second bottoms stream; and
recycling the second overhead stream into the distillation column.

11. The method of claim 1 further comprising:
performing polymerizing the monomer and the comonomer and separating the product stream occur in parallel in two or more reaction zones and corresponding separation zones; and
wherein two or more of the unreacted components streams corresponding to the two or more reaction zones and corresponding separation zones are combined before separating the unreacted components stream.

12. The method of claim 1, wherein the monomer comprises ethylene, the comonomer comprises 1-hexene, and the inert isomer/saturate of the comonomer comprises hexane.

13. The method of claim 1, wherein the monomer comprises ethylene, the comonomer comprises 1-octene, and the inert isomer/saturate of the comonomer comprises octane.

14. The method of claim 1, wherein the monomer comprises propylene, the comonomer comprises 1-hexene, and the inert isomer/saturate of the comonomer comprises hexane.

15. The method of claim 1, wherein the monomer comprises propylene, the comonomer comprises 1-octene, and the inert isomer/saturate of the comonomer comprises octane.

16. The method of claim 1, wherein polymerizing occurs further in the presence of an inert C5− hydrocarbon.

17. The method of claim 16, wherein the C5− inert hydrocarbon comprises propane, n-butane, i-butane, n-pentane, i-pentane, and any combination thereof.

18. A system comprising:
a polymerization reactor fluidly coupled to a polymer separation zone configured to receive a product stream from the polymerization reactor and separate the polymer product into two or more streams comprising: (a) a polymer stream comprising a polymer and (b) an unreacted components stream comprising (i) an unreacted monomer, (ii) an unreacted comonomer, and (iii) an inert isomer/saturate of the comonomer, wherein the inert isomer/saturate of the comonomer is an inert isomer of the comonomer, a saturate of the comonomer, or a combination thereof; and an unreacted components separation zone fluidly coupled to the polymer separation zone and configured to receive the unreacted components stream from the polymer separation zone and separate the unreacted components stream into two or more streams comprising: (a) an overhead stream comprising the unreacted monomer and (b) a bottoms stream comprising the comonomer and the inert isomer/saturate of the comonomer, wherein a concentration of C5− hydrocarbons in the overhead stream is higher than a concentration of the C5− hydrocarbons in the unreacted components stream, and wherein a concentration of C6+ hydrocarbons in the bottoms stream is higher than a concentration of the C6+ hydrocarbons in the unreacted components stream;

wherein the polymerization reactor is fluidly coupled to the unreacted components separation zone and configured to receive the overhead stream from the unreacted components separation zone;

further wherein the unreacted components separation zone comprises a distillation column fluidly coupled to the polymer separation zone and configured to receive the unreacted components stream from the polymer separation zone, wherein the overhead stream is a first overhead stream, and wherein the unreacted components separation zone comprises a condenser fluidly coupled to the distillation column and configured to receive a second overhead stream from the distillation column and produce the first overhead stream.

19. The system of claim 18, wherein the bottoms stream is a first bottoms stream, and the unreacted components separation zone comprises a reboiler configured to receive a second bottoms stream from the distillation column and produce (a) a vapor bottoms stream and (b) a liquid bottoms stream, wherein the distillation column is also configured to receive the vapor bottoms stream from the reboiler.

* * * * *